US009314544B2

(12) United States Patent
Catalan et al.

(10) Patent No.: US 9,314,544 B2
(45) Date of Patent: Apr. 19, 2016

(54) DURABLE HYDROPHILIC COATING COMPOSITIONS

(76) Inventors: Kemal Vatansever Catalan, Cincinnati, OH (US); Carolyn Ann Spitzmueller, Cincinnati, OH (US); Vladimir Gartstein, Mason, OH (US); Matthew Scott Wagner, Cincinnati, OH (US); Dennis Ray Bacon, Cincinnati, OH (US); David S. Salloum, West Chester, OH (US); Faiz Feisal Sherman, Mason, OH (US)

( * ) Notice: Subject to any disclaimer, the term of this patent is extended or adjusted under 35 U.S.C. 154(b) by 1716 days.

(21) Appl. No.: 12/191,339

(22) Filed: Aug. 14, 2008

(65) Prior Publication Data

US 2009/0048571 A1 Feb. 19, 2009

Related U.S. Application Data

(60) Provisional application No. 60/965,225, filed on Aug. 17, 2007.

(51) Int. Cl.
| | |
|---|---|
| *A61F 13/15* | (2006.01) |
| *A61F 13/20* | (2006.01) |
| *A61L 15/42* | (2006.01) |
| *A61L 15/22* | (2006.01) |

(52) U.S. Cl.
CPC .................. *A61L 15/42* (2013.01); *A61L 15/22* (2013.01); *A61L 2400/12* (2013.01)

(58) Field of Classification Search
USPC .............................. 604/365, 367, 385.01, 378
See application file for complete search history.

(56) References Cited

U.S. PATENT DOCUMENTS

| | | | |
|---|---|---|---|
| 3,860,003 | A | 1/1975 | Buell |
| 3,929,678 | A | 12/1975 | Laughlin et al. |
| 4,469,746 | A | 9/1984 | Weisman et al. |
| 4,940,464 | A | 7/1990 | Van Gompel et al. |
| 5,092,861 | A | 3/1992 | Nomura et al. |
| 5,137,537 | A | 8/1992 | Herron et al. |
| 5,151,092 | A | 9/1992 | Buell |
| 5,246,433 | A | 9/1993 | Hasse et al. |
| 5,554,145 | A | 9/1996 | Roe et al. |
| 5,569,234 | A | 10/1996 | Buell et al. |
| 5,576,282 | A | 11/1996 | Miracle et al. |
| 5,707,950 | A | 1/1998 | Kasturi et al. |
| 5,897,545 | A | 4/1999 | Kline et al. |
| 5,957,908 | A | 9/1999 | Kline et al. |

(Continued)

FOREIGN PATENT DOCUMENTS

| | | |
|---|---|---|
| CN | 1 644 639 A | 7/2005 |
| WO | WO 2004/071340 A2 | 8/2004 |
| WO | WO 2007/106398 A2 | 9/2007 |

OTHER PUBLICATIONS

International Search Report, Dated Mar. 8, 2010, 5 pages.

*Primary Examiner* — Michele M Kidwell
(74) *Attorney, Agent, or Firm* — Wednesday G. Shipp; Andrew A Paul

(57) ABSTRACT

A durable hydrophilic coating composition is provided comprising a film forming polymer, a wetting agent and from about 0.001% to about 40%, by weight of the composition, of nanoparticles. The nanoparticles are selected from the group consisting of alumina, silica and combinations thereof and have a particle size of from about 1 to about 750 nanometers. The weight ratio of the film forming polymer to the nanoparticles is from about 1:1 to about 1:30. A disposable absorbent article is also disclosed.

13 Claims, 8 Drawing Sheets

(56) References Cited

U.S. PATENT DOCUMENTS

| | | |
|---|---|---|
| 6,004,306 A | 12/1999 | Robles et al. |
| 6,120,487 A | 9/2000 | Ashton |
| 6,120,489 A | 9/2000 | Johnson et al. |
| 2002/0151634 A1* | 10/2002 | Rohrbaugh et al. .......... 524/430 |
| 2003/0233082 A1 | 12/2003 | Kline et al. |
| 2004/0034157 A1 | 2/2004 | Ghosh et al. |
| 2004/0158213 A1* | 8/2004 | Ponomarenko et al. ...... 604/367 |
| 2007/0275929 A1* | 11/2007 | Fuls et al. ...................... 514/75 |
| 2009/0318598 A1* | 12/2009 | Perez et al. ................... 524/261 |

* cited by examiner

DURABLE HYDROPHILIC COATING COMPOSITIONS

CROSS REFERENCE TO RELATED APPLICATION(S)

This application claims the benefit of U.S. Provisional Application No. 60/965,225, filed Aug. 17, 2007.

FIELD OF THE INVENTION

The present disclosure relates to durable hydrophilic coating compositions. The present disclosure also relates to absorbent articles, and more particularly to a disposable absorbent article with a durable hydrophilic core wrap. The present disclosure also relates to methods of preparing durable hydrophilic coating compositions and coated-treated nonwovens.

BACKGROUND OF THE INVENTION

Disposable absorbent articles such as diapers, training pants, adult incontinence products and feminine care products are well known in the art. Such disposable articles collect and retain urine and fecal material deposited thereon by the wearer.

Nonwoven fabrics made of synthetic fibers and/or natural fibers are commonly used in absorbent articles, for example, as topsheet material or as core wrap to enclose the storage layer of the absorbent core. Such nonwoven fabrics are usually hydrophobic. However, for many applications in hygiene products it is necessary to have hydrophilic nonwovens. Therefore, the nonwoven fabric has to be treated accordingly. One typical component of disposable absorbent articles is core wraps. A core wrap is typically a nonwoven material which has been rendered hydrophilic and designed to contain the storage layer and provide structural integrity when the storage layer is wet or dry. Core wraps may also be a tissue wrap.

A common method for rendering nonwoven fabrics hydrophilic or ensuring hydrophilicity is coating the surface of the nonwoven with hydrophilic surfactants. As this coating does not lead to a tight chemical bond between the nonwoven and the surfactant, coating of this type are not sufficiently durable and the surfactant can be washed off during use when the absorbent article is wetted. The decrease in liquid strike-through time is a desirable effect when the nonwoven is coated with surfactant. Liquid strike-through refers to liquid passing through the nonwoven fabric with liquid strike-through time referring to the time it takes for a certain amount of liquid to pass through the nonwoven. However, as the surfactant is washed off when coated nonwoven fabrics are exposed to the liquid, the strike-through time in successive gushes is increased. This results in performance reduction during use on diapers or other articles comprising such nonwoven fabrics. Furthermore, at the same time as liquid strike-through time decreases due to surfactant wash-off, surface tension of the liquid, which was in contact with the nonwoven fabric, is also reduced. This reduction is undesirable, because it can cause increased urine leakage in a diaper. Increasing the add-on levels of surfactants does not solve strike-through time problem. Rather, the increased add-on levels typically result in dry migration of the surfactants to other areas of the diaper, such as the barrier leg cuffs and additional surface tension reduction of the fluid to be absorbed. Thus, increased surfactant levels to render nonwovens hydrophilic can lead to multiple negative impacts when incorporated into an absorbent hygiene article.

Another common method to render a nonwoven fabric hydrophilic is by applying corona and/or plasma treatment. Plasma is an ionized form of gas that can be obtained by ionizing a gas or liquid medium. Plasmas are widely used for the treatment of organic and inorganic materials to promote adhesion between various materials. Polymers that have chemically inert surfaces with low surface energies do not allow good coatings with bondings and adhesives. Thus, these surfaces are treated to make them receptive to bonding with other substrates, coatings, adhesives and printing inks. However, corona and plasma treatments lead to low coating durability upon storage of the treated material, i.e., hydrophilicity decreases over time.

Accordingly, there is a need for a hydrophilic coating of a nonwoven, which is durable upon storage, does not migrate or transfer easily when dry or subjected to elevated temperature of storage, is not easily washed off when wetted or when fluid passes through or is in contact with the nonwoven, achieves a fast liquid strike-through time, both initially and following multiple exposures to aqueous fluids or liquids, does not lower the surface tension of the fluid to be absorbed below 55 dynes/cm, and is not easily abraded or rubbed off the surface.

SUMMARY OF THE INVENTION

Other features and advantages of the invention may be apparent from reading the following detailed description, drawings, and claims.

In one embodiment, a durable hydrophilic coating composition includes a film forming polymer; a wetting agent; and from about 0.001% to about 40%, by weight of the composition, of nanoparticles, wherein the nanoparticles are selected from the group consisting of alumina, silica and combinations thereof and wherein the nanoparticles have a particle size of from about 1 to about 750 nanometers. The weight ratio of the film forming polymer to the nanoparticles is from about 1:1 to about 1:30.

In another embodiment, a disposable absorbent article includes an absorbent core. The absorbent core includes a storage layer; and a hydrophilic fluid pervious core wrap, the core wrap surrounding at least a portion of the storage layer. The core wrap includes a core wrap substrate; and a durable hydrophilic coating composition coated on the core wrap substrate. The coating composition includes a film forming polymer, a wetting agent, and from about 0.001% to about 40%, by weight of the composition, of nanoparticles wherein the nanoparticles are selected from the group consisting of alumina, silica and combinations thereof and wherein the nanoparticles have a particle size of from about 1 to about 750 nanometers. The weight ratio of the film forming polymer to the nanoparticles is from about 1:1 to about 1:30.

DETAILED DESCRIPTION OF THE INVENTION

Figure 1:
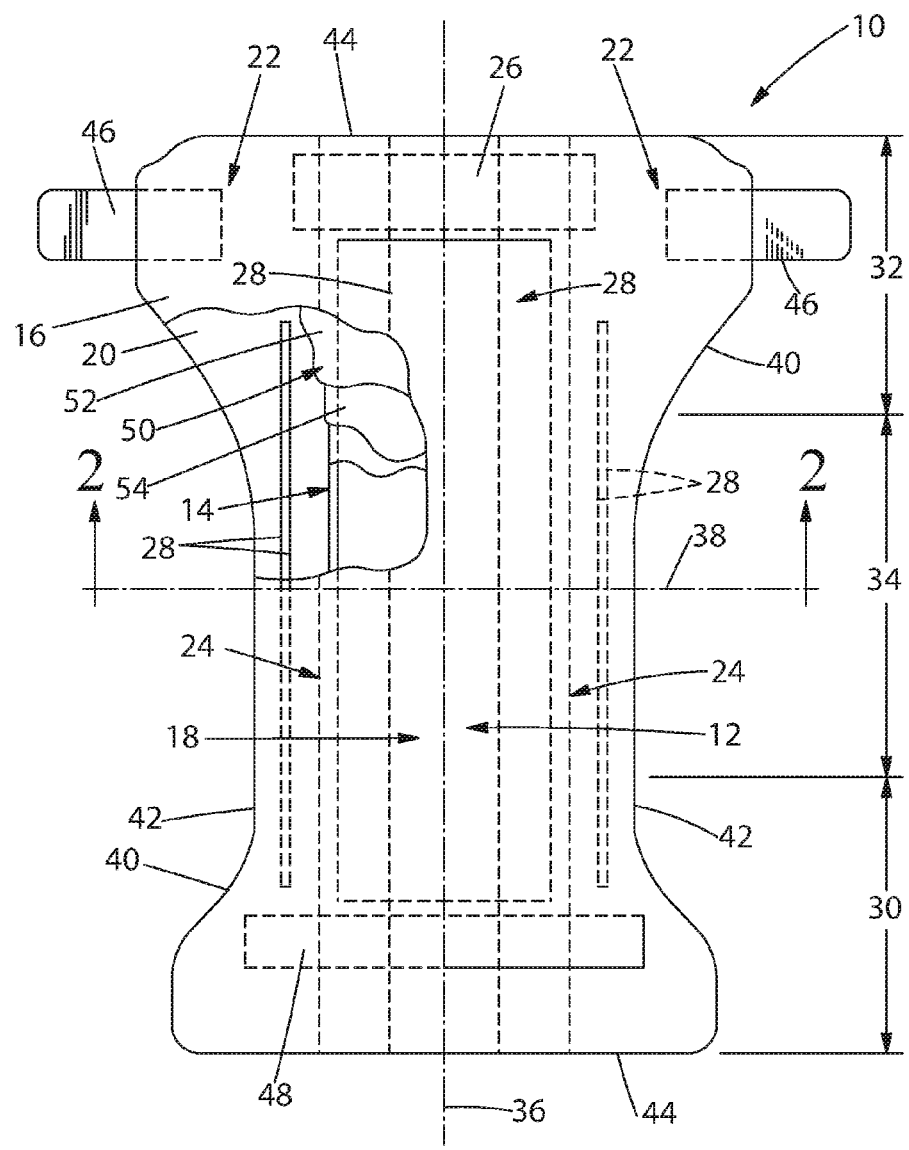
FIG. 1 is a plan view of an exemplary disposable absorbent article in accordance with an embodiment of the present disclosure.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, pet pads and the like. As used herein, the term "body fluids" or "body exudates" includes, but is not limited to, urine, blood, vaginal discharges, breast milk, sweat and fecal matter.

"Coating" includes coatings that completely cover a surface, or portion thereof (for example, continuous coatings, including those that form films on the surface), as well as coatings that may only partially cover a surface, such as those coatings that after drying leave gaps in coverage on a surface (for example, discontinuous coatings). The later category of coatings may include, but is not limited to, a network of covered and uncovered portions and distributions of particles and nanoparticles on a surface which may have spaces between the particles or nanoparticles. In some embodiments, the coating forms at least one layer of nanoparticles or continuous film on the surface which has been coated, and is substantially uniform. However, when the coatings described herein are described as being applied to a surface, it is understood that the coatings need not be applied to, or that they cover the entire surface. For instance, the coatings will be considered as being applied to a surface even if they are only applied to modify a portion of the surface.

"Comprise," "comprising," and "comprises" are open ended terms, each specifies the presence of what follows, e.g., a component, but does not preclude the presence of other features, for example, elements, steps, components known in the art, or disclosed herein.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Durable hydrophilic coating" means a composition when coated on a nonwoven, such as a core wrap substrate to make a hydrophilic fluid pervious core wrap, produces a durable hydrophilic fluid pervious core wrap which has a liquid strike-through time for the first gush of less than or equal to about 6 seconds, and in another embodiment less than or equal to about 4 seconds, and has a liquid strike-through time for the fifth gush of test liquid, of less than or equal to about 6 seconds, in another embodiment of less than or equal to about 4 seconds, when tested in accordance with the Strike-Through Test in the Test Methods section and further described herein. Additionally, "durable hydrophilic coating" means a composition when coated on a nonwoven, such as a core wrap substrate to make a hydrophilic fluid pervious core wrap, produces a durable hydrophilic fluid pervious core wrap which does not migrate along the surface of the nonwoven or coated surface nor transfer from one surface to an adjacent surface during storage or elevated temperatures when tested in accordance with the test methods described in the Test Methods section and further described herein.

"Hydrophilic" describes fibers or surfaces of fibers, which are wettable by aqueous fluids (for example, aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin or combination and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (for example, side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

Exemplary Absorbent Article

FIG. 1 is a plan view of an exemplary disposable absorbent article 10, such as a diaper, according to the present disclosure. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a top sheet 18, which may be liquid pervious, and/or a back sheet 20, which may be liquid impervious. The absorbent core 14 may be encased between the top sheet 18 and the back sheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are for example, described in U.S. Pat. No. 3,860,003 and U.S. Pat. No. 5,151,092.

For unitary absorbent articles, the chassis 12 and absorbent core 14 may form the main structure of the diaper 10 with other features added to form the composite diaper structure. While the top sheet 18, the back sheet 20, and the absorbent core 14 may be assembled in a variety of well-known configurations, exemplary diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

According to a certain embodiment, diaper 10 may also comprise an acquisition system 50 disposed between the liquid permeable top sheet 18 and a wearer facing side of the absorbent core 14. The acquisition system 50 may be in direct contact with the absorbent core. The acquisition system 50 may comprise a single layer or multiple layers, such as an upper acquisition layer 52 facing the towards the wearer's skin and a lower acquisition 54 layer facing the garment of the wearer. According to a certain embodiment, the acquisition system 50 may function to receive a surge of liquid, such as a gush of urine, and quickly absorb the liquid and distribute it across the absorbent core 14 so that the absorbent core absorbs the liquid before the liquid flows beyond the absorbent layer 14 and out of the diaper 10. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537.

In a certain embodiment, one or both of the upper and lower acquisition layers 52 and 54 may comprise a nonwoven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

Core Wrap Substrate

As illustrated in the embodiments shown in FIGS. 2-5, the hydrophilic core wrap provides a substrate which has both an extended shelf life and wear life. Prior high-energy treatments tended to have a short shelf life. That is, during the time from purchase to ultimate use and disposal by the consumer the substrate would trend to loose its hydrophilicity. Surfactant treatments, such as those of the prior art, on the other hand would often have an adequate shelf life, but have an inadequate wear life. That is, upon contact with bodily fluids, such as urine, the substrate would instantly begin to lose its hydrophilic properties. This may even lead to a surface which repels the bodily fluids it is designed to absorb even though the absorbent article has not reached its total absorbance capacity. Additionally, surfactant treatments would migrate in the dry state from the core wrap substrate to other areas of the diaper, such as the barrier leg cuff. This dry migration or transfer of surfactant from the core nonwoven to the cuff nonwoven results in a compromised barrier leg cuff which leads to leakage.

Figure 2:
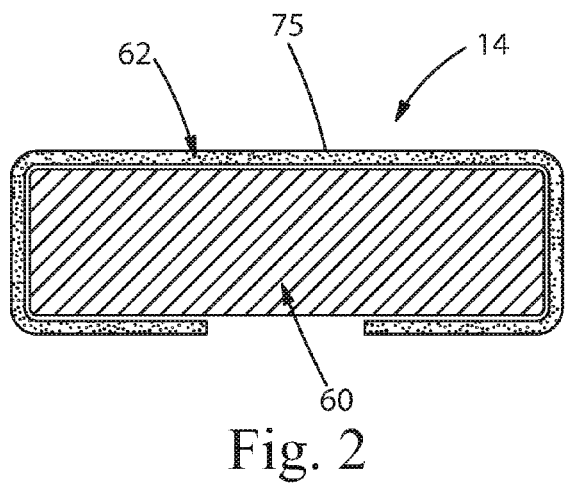
FIG. 2 is a partial sectional view along sectional line 2-2 of one exemplary embodiment of the absorbent core of the disposable absorbent article shown in FIG. 1.

FIG. 2 is a sectional view along 2-2 showing a section of one alternative embodiment of the absorbent core 14 of the diaper of FIG. 1. In FIG. 2 a storage layer 60 is wrapped by a core wrap 62 in a C-fold. The core wrap 62 comprises a substrate which has been coated with a durable hydrophilic coating composition. The substrate may be a nonwoven, a polymeric film or combinations thereof.

Figure 3:
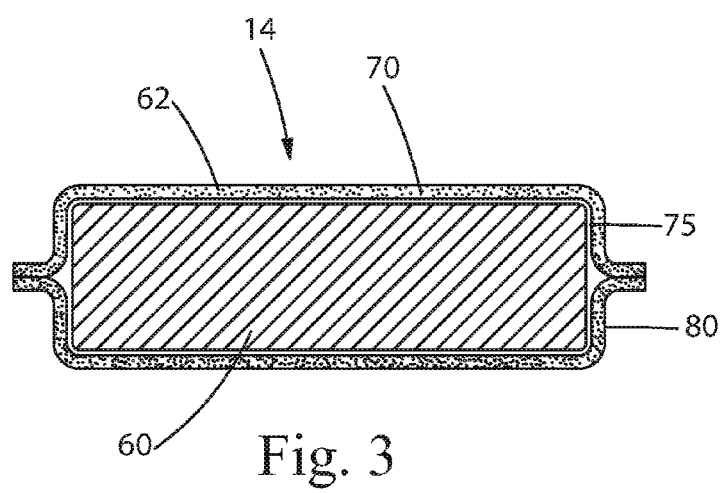
FIG. 3 is a partial sectional view along sectional line 2-2 of another exemplary embodiment of the absorbent core of the disposable absorbent article shown in FIG. 1.

FIG. 3 is a sectional view along 2-2 showing a section of one alternative embodiment of the absorbent core 14 of the diaper of FIG. 1. In FIG. 3 the storage layer 60 is surrounded or enveloped by the core wrap 62. The core wrap 62 comprises a fluid receiving top layer or substrate 70 and a bottom layer or substrate 80. The fluid receiving top layer 70 and the bottom layer 80 can be same or different. That is they may be the same substrate coated with the same durable hydrophilic coating composition, the different substrates coated with the same durable hydrophilic coating composition or different substrates coated with different durable hydrophilic coating compositions. The top layer 70 of the storage layer 60 may be referred to as a core cover and the bottom layer 80 of the storage layer 60 may be referred to as a dusting layer. In one embodiment, the top layer 70 and the bottom layer 80 may comprise non-woven material. One exemplary material is a SMS material, comprising a spunbonded, a melt-blown and a further spunbonded layer. The top layer 70 and the bottom layer 80 may be provided from two or more separate sheets of nonwoven materials or they may be alternatively provided from a unitary sheet of material. SMS materials are exemplified in more detail herein.

Figure 4:
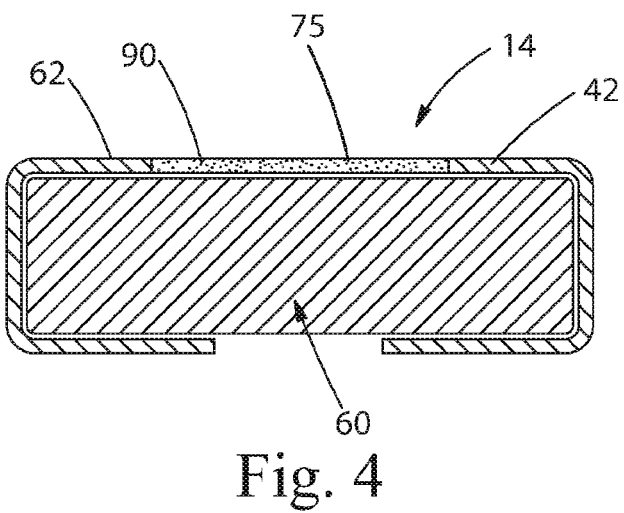
FIG. 4 is a partial sectional view along sectional line 2-2 of another exemplary embodiment of the absorbent core of the disposable absorbent article shown in FIG. 1.
Figure 5:
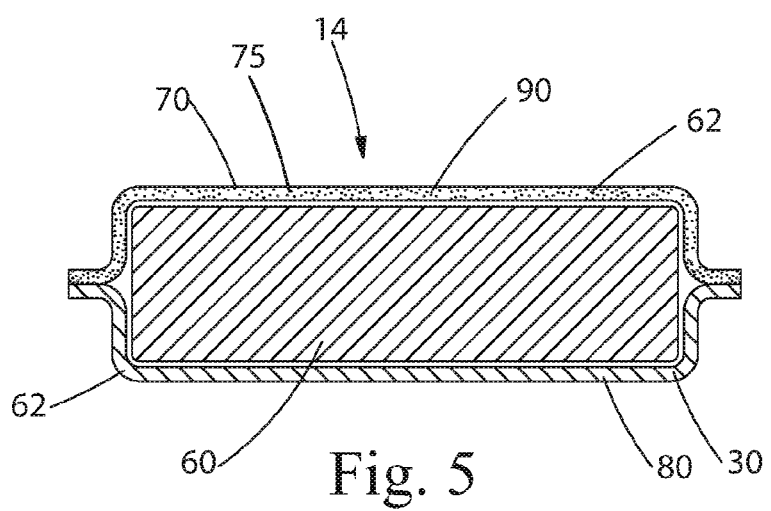
FIG. 5 is a partial sectional view along sectional line 2-2 of another exemplary embodiment of the absorbent core of the disposable absorbent article shown in FIG. 1.

In alternative embodiments as shown in FIGS. 4 and 5, only a portion of the core wrap substrate 62 is coated with the durable hydrophilic coating composition. FIG. 4 is a sectional view along 2-2 showing a section of the absorbent core 14 of the diaper of FIG. 1. In FIG. 4 the storage layer 60 is wrapped by a core wrap substrate 62 in a C-fold. The core wrap substrate 62 comprises two portions: a portion which has been coated with the durable hydrophilic coating composition, or coated portion 90, and a portion which is not coated with the durable hydrophilic coating composition, or uncoated portion 92. FIG. 5 is a sectional view along 2-2 showing a section of one alternative embodiment of the absorbent core 14 of the diaper of FIG. 1. In FIG. 5 the storage layer 60 is surrounded or enveloped the core wrap substrate 62. The core wrap substrate 62 comprises a top layer 70, which has been coated with the durable hydrophilic coating composition, and forms a coated portion 90; and a bottom layer 80 which is not coated with the durable hydrophilic coating composition, and forms an uncoated portion 92.

In another embodiment the uncoated portion 92 may be coated with a different composition to give it different physical properties than that of the coated portion 90. For example, the uncoated portion 92 may be coated with a composition to make it more hydrophobic, or it may be coated with a durable hydrophilic coating composition different than that used to coat the coated portion 90. In one embodiment, the hydrophilic core wrap will have a basis weight of between about 1 grams per square meter (or gsm) and about 100 gsm, in another embodiment between about 2 gsm and about 50 gsm, and in yet another embodiment between about 5 gsm and about 30 gsm.

In one embodiment, the core wrap substrate 62 may comprise any known type of substrate, including but not limited to fabrics, garments, textiles, and films. In certain embodiments, the substrate may comprise one or more fibers. A fiber is defined as a fine hairlike structure, of animal, vegetable, mineral, or synthetic origin. Commercially available fibers have diameters ranging from less than about 0.001 mm (about 0.00004 in) to more than about 0.2 mm (about 0.008 in) and they come in several different forms: short fibers (known as staple, or chopped), continuous single fibers (filaments or monofilaments), untwisted bundles of continuous filaments (tow), and twisted bundles of continuous filaments (yarn).

The substrate may comprise fibers made by nature (natural fibers), made by man (synthetic or man-made), or combinations thereof. Non-limiting examples of natural fibers include animal fibers such as wool, silk, fur, and hair; vegetable fibers such as cellulose, cotton, flax, linen, and hemp; and certain naturally occurring mineral fibers. Synthetic fibers can be derived from natural fibers or not. For example, synthetic fibers which are derived from natural fibers, include but are not limited to, rayon and lyocell, both of which are derived from cellulose. Synthetic fibers which are not derived from natural fibers can be derived from other natural sources or from mineral sources. Non-limiting examples of synthetic fibers derived from natural sources include polysaccharides such as starch. Non-limiting examples of fibers from mineral sources include polyolefin fibers such as polypropylene and polyethylene fibers, which are derived from petroleum, and silicate fibers such as glass and asbestos. Synthetic fibers are commonly formed, when possible, by fluid handling processes (for example, extruding, drawing, or spinning a fluid such as a resin or a solution). Synthetic fibers are also formed by solid handling size reduction processes (for example, mechanical chopping or cutting of a larger object such as a monolith, a film, or a fabric).

Examples of suitable synthetic fibers which may comprise all or part of the core wrap substrates of the present disclosure include but are not limited, to nylon (polyamide), acrylic (polyacrylonitrile), aramid (aromatic polyamide), polyolefin (polyethylene and polypropylene), polyester, butadiene-styrene block copolymers, natural rubber, latex, spandex (polyurethane) and combinations thereof.

Synthetic fibers that contain more than one type of repeat unit can result from combining repeat units at the molecular level within each macromolecular strand (co-polymer), between macromolecular strands (homopolymer blends), or combinations thereof (co-polymer blends); or they can result from combining repeat units at a higher scale level with distinct nanoscopic, microscopic, or macroscopic phases (for example, multicomponent fibers). Each component of a multicomponent fiber can comprise a homopolymer, a co-polymer, or blends thereof. Bicomponent fibers are common versions of multicomponent fibers. The two or more types of repeat units in a copolymer can be arranged randomly or in alternating blocks of each type. Blocks of different types of repeat units can joined to one another at their respective ends (block co-polymers) or between the respective end of at least one block (graft co-polymers).

Nonwoven materials are a type of fabric typically made from fibers in a web format. Nonwoven materials are described by Butler I, Batra S K, et al, Nonwovens Fabrics Handbook, Association of the Nonwoven Fabrics Industry, 1999, and by Vaughn E A, Nonwoven Fabric Sampler and Technology Reference, Association of the Nonwoven Fabrics Industry.

Substrates comprising nonwoven materials can be formed by direct extrusion processes during which the fibers and the nonwoven materials are formed at about the same point in time, or by preformed fibers which can be laid into nonwoven materials at a distinctly subsequent point in time. Exemplary direct extrusion processes include but are not limited to: spunbonding, meltblowing, solvent spinning, electrospinning, and combinations thereof typically forming layers. Exemplary "laying" processes include wetlaying and drylaying. Example drylaying processes include, but are not limited to, airlaying, carding, and combinations thereof typically forming layers. Combinations of the above processes yield nonwovens commonly called hybrids or composites. Exemplary combinations include, but are not limited to, spunbond-meltblown-spunbond (SMS), spunbond-carded (SC), spunbond-airlaid (SA), meltblown-airlaid (MA), and combinations thereof, typically in layers. Combinations which include direct extrusion can be combined at the about the same point in time as the direct extrusion process (for example, spinform and coform for SA and MA), or at a subsequent point in time. In the above examples, one or more individual layers can be created by each process. For instance, SMS can mean a three layer, 'sms' nonwoven materials, a five layer 'ssmms' nonwoven materials, or any reasonable variation thereof wherein the lower case letters designate individual layers and the upper case letters designate the compilation of similar, adjacent layers.

The fibers in nonwoven materials are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers and nonwoven materials can be subjected to additional treatment after formation. For nonwoven materials, additional treatment commonly occurs after the fibers are joined to one another (post-treatment). Examples of additional treatments include, but are not limited to, mechanical stresses, chemical additives, or combinations thereof. In another embodiment, the term "core wrap substrate" may include laminates of two or more substrates or webs. Additionally, the substrates may be flat or textured.

Durable Hydrophilic Coating Composition

According to one embodiment, the durable hydrophilic coating composition includes (a) a film forming polymer; (b) a wetting agent; and (c) nanoparticles. The coating composition is coated onto a nonwoven. In one embodiment, the nonwoven is core wrap substrate 62 in an amount which provides the desired hydrophilicity and durability, i.e. a core wrap which has a liquid strike-through time for the first gush of less than or equal to about 6 seconds, in another embodiment less than or equal to about 4 seconds, and has a liquid strike-through time for the fifth gush of test liquid, of less than or equal to about 6 seconds, in another embodiment of less than or equal to about 4 seconds, when tested in accordance with the Strike-Through Test in the Test Methods section and further described herein.

Typically the amount of coating composition present on the nonwoven will vary depending upon many factors, including but not limited to, the nonwoven used, the film forming polymer used, the wetting agent used, the nanoparticles used, the manner of applying the coating composition, the desired hydrophilicity of the nonwoven, the consumer product in which the absorbent core is used, etc. In one embodiment, the amount of hydrophilic coating composition on the nonwoven substrate will be between about 0.001 grams per square meter of substrate (or gsm substrate) and about 30 gsm substrate, in another embodiment between about 0.01 gsm substrate and about 20 gsm substrate, and in yet another embodiment between about 0.1 gsm substrate and about 10 gsm substrate.

Figure 6:
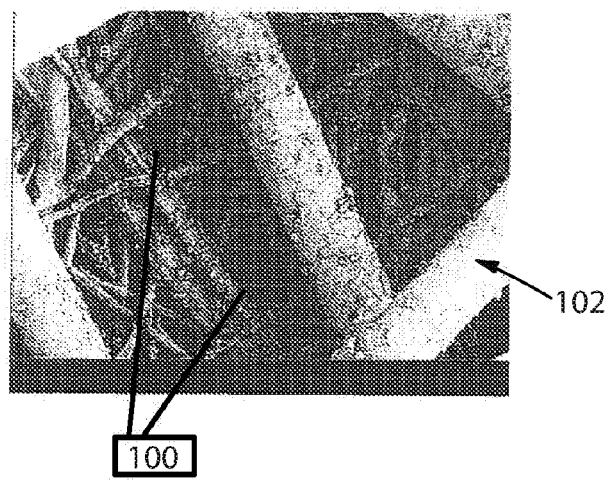
FIG. 6 is a scanning electron microscope image of the durable hydrophilic coating composition in accordance with an embodiment of the present disclosure.

As illustrated in FIG. 6, the durable hydrophilic coating is a solid in the dry state. As can be seen, nanoparticles 100 can be seen embedded in the film forming polymer 102. Without wishing to be bound by theory, it has been found that this type of durable coating does not migrate in the dry state.

Film Forming Polymer

In one embodiment, the durable hydrophilic coating compositions comprise a film forming polymer. While not intending to be bound by theory, it is believed that the film forming polymer serves as a binding surface to fix in place the nanoparticles.

Film forming polymers that are suitable for use in the coating compositions include, but are not limited to, polyamines, quatemized polyamines, zwitterionic polymers; polycarboxylates; polyethers; polyhydroxylated polymers; polyphosphonates and polyphosphates; polymeric chelants; ethoxylated or alkoxylated polyamines; polycarboxylated polyamines; water dispersible polyethers; water dispersible polyhydroxylated groups or polymers, including polysaccharides; water dispersible polycarboxylates; water dispersible anionic groups such as carboxylates, sulfonates, sulfates, phosphates, phosphonates and polymers thereof; dispersible polystyrenes containing anionic groups such as carboxylates, sulfonates, sulfates, phosphates, phosphonates and polymers thereof; water dispersible polymers containing groups of amines, quaternaries, amine oxides and combinations thereof; water dispersible zwitterionic groups and polymers thereof; water dispersible amides and polyamides; and water dispersible polymers and copolymers of vinylimidazole and vinylpyrrolidone. Polymer and block co-polymer combinations of the above.

In one embodiment, film forming polymers are typically employed in compositions at levels of from about 0.1% to about 60%, in another embodiment at levels of from about 1% to about 30%, and in yet another embodiment at levels of from about 5% to about 20%, by weight of the composition.

In one embodiment, the film forming polymer is a sodium polystyrene sulfonate sold under the trade name "FLEXAN II" by National Starch. In another embodiment, the film forming polymer is a high Mw sodium polystyrene sulfonate sold under the trade name "Versa-TL", for example, 501, 502, by Alco Chemicals. In another embodiment, the film forming polymer is a Polyvinylpolypyrrolidone sold under the tradename "PVP K3" by ISP. In another embodiment, the film-forming polymer is a polyvinylimine sold under the tradename "LUPAMIN 9095", by BASF. In another embodiment, the film-forming polymer and rheology modifier is Xanthan gum sold under the tradename "KELZAN ASX", by C. P. Kelco. In another embodiment, the film-forming polymer and rheology modifier is Hydroxypropylcellulose, sold under the tradename "KLUCEL", by Hercules, Inc.

Wetting Agent

The durable hydrophilic coating compositions also comprise a wetting agent to facilitate the dispersion of nanoparticles onto the substrate. In one embodiment, surfactants are used as wetting agents. As one example, surfactants are included when the coating composition is used to treat a hydrophobic substrate. For concentrated compositions, the surfactant can facilitate the dispersion of many adjunct ingredients such as antimicrobial actives and perfumes in the concentrated aqueous compositions.

Suitable surfactants can be selected from the group including anionic surfactants, cationic surfactants, nonionic surfactants, amphoteric surfactants, ampholytic surfactants, zwitterionic surfactants and mixtures thereof. Nonlimiting examples of surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); U.S. Pat. Nos. 5,707,950 and 5,576,282; and U.S. Pat. No. 3,929,678, to Laughlin et al., issued Dec. 30, 1975.

When a surfactant is used in the coating composition, it may be added at an effective amount to facilitate application of the coating composition. Surfactant is typically employed in compositions at levels of from about 0.0001% to about 60%, in another embodiment at levels of from about 0.001% to about 35%, and in yet another embodiment at levels of from about 0.001% to about 25%, by weight of the composition.

Nonlimiting examples of surfactants, include nonionic and amphoteric surfactants such as Gemini diol ethoxylates, nonionic surfactants of Hydrophilic-Lipophilic Balance (HLB) between 3 and 16, the $C_{12}$-$C_{18}$ alkyl ethoxylates ("AE") including the narrow peaked alkyl ethoxylates and $C_6$-$C_{12}$ alkyl phenol alkoxylates (for example, ethoxylates and mixed ethoxy/propoxy), $C_{12}$-$C_{18}$ betaines and sulfobetaines ("sultaines"), $C_{10}$-$C_{18}$ amine oxides, and the like. In one embodiment, the wetting agent is a nonionic surfactant sold under the trade name "DYNOL 604" by Air Products and Chemical, Inc. In another embodiment, the wetting agent is a nonionic surfactant sold under the trade name "DYNOL 607" by Air Products and Chemical, Inc. In another embodiment, the wetting agent is a nonionic surfactant sold under the tradename SURFYNOL™, by Air Products and Chemical, Inc, for example, Surfynol 420, Surfynol 440, Surfynol 465, Surfynol 485. In another embodiment, the wetting agent is a nonionic surfactant sold under the tradename CARBOWET, by Air Products and Chemical, Inc, e.g., Carbowet 106, Carbowet 109. And, in another embodiment, the wetting agent is a nonionic surfactant sold under the tradename NEODOL, by Shell Chemicals, for example, Neodol 91-6, Neodol 23-3, Neodol 1-9, Neodol 1-7, Neodol 91-8, Neodol 45-7, and mixtures of above.

Another class of useful surfactants is silicone surfactants and/or silicones. They can be used alone and/or alternatively in combination with the alkyl ethoxylate surfactants described herein. Nonlimiting examples of silicone surfactants are the polyalkylene oxide polysiloxanes having a dimethyl polysiloxane hydrophobic moiety and one or more hydrophilic polyalkylene side chains, and having the general formula:

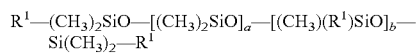

wherein a+b are from about 1 to about 50, and each $R^1$ is the same or different and is selected from the group consisting of methyl and a poly(ethyleneoxide/propyleneoxide) copolymer group having the general formula: —$(CH_2)_nO(C_2H_4O)_c$ $(C_3H_6O)_dR^2$, wherein n is 3 or 4; total c (for all polyalkyleneoxy side groups) has a value of from 1 to about 100, alternatively from about 6 to about 100; total d is from 0 to about 14; alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group, alternatively hydrogen and methyl group. Each polyalkylene oxide polysiloxane has at least one $R^1$ group being a poly(ethyleneoxide/propyleneoxide) copolymer group. Silicone superwetting agents are available from Dow Corning as silicone glycol copolymers (for example, Q2-5211 and Q2-5212) and from Degussa, sold under the tradename TEGOWET.

It is also within the scope of the present disclosure to use a mixture of surfactants.

Nanoparticles

The durable hydrophilic coating compositions also comprise nanoparticles and optionally larger size aggregate clusters of nanoparticles to provide permanent hydrophilicity or increase surface energy.

Nanoparticles are particles which have a particle size ranging from about 1 to about 5000 nanometers. Such particles are technologically significant since they are utilized to produce durable hydrophilic coatings that have novel and useful properties due to the very small dimensions of their particulate constituents. Nanoparticles with particle sizes ranging from about 2 nm to about 750 nm can be economically produced. Non-limiting examples of particle size distributions of the nanoparticles are those that fall within the range from about 2 nm to less than about 750 nm, alternatively from about 2 nm to less than about 200 nm, and alternatively from about 2 nm to less than about 150 nm. The nanoparticles are present in the coating compositions at levels of from about 0.1% to about 60%, in another embodiment at levels of from about 1% to about 30%, and in yet another embodiment at levels of from about 5% to about 20%, by weight of the composition.

The particle size of the nanoparticles is the largest diameter of a nanoparticle and may be measured by any conventional method.

The mean particle size of various types of nanoparticles may differ from the particle size distribution of the nanoparticles particles. For example, a layered synthetic silicate can have a mean particle size of about 25 nanometers while its particle size distribution can generally vary between about 10 nm to about 40 nm. (It should be understood that the particle sizes that are described herein are for particles when they are dispersed in an aqueous medium and the mean particle size is based on the mean of the particle number distribution. Non-limiting examples of nanoparticles can include crystalline or amorphous particles with a particle size from about 2 to about 750 nanometers. Boehmite alumina can have an average particle size distribution from 2 to 750 nm.)

Either organic or inorganic nanoparticles may be used. Suitable organic nanoparticle include, but are not limited to, dendrimers with surface groups such as poly(amidoamine) (PAMAM) phosphorous, and polypropylenimine; silsesquioxane polymers; polystyrene; polymethyl methacrylate; polyethylene; nylon; melamine (polymethylenemelamine); polyactide; dextran; chitosan, and nanolatexes. A "nanolatex", as used herein, is a latex with particle sizes less than or equal to about 750 nm. A "latex" is a colloidal dispersion of water-insoluble polymer particles that are usually spherical in shape. Nanolatexes may be formed by emulsion polymerization. "Emulsion polymerization" is a process in which monomers of the latex are dispersed in water using a surfactant to form a stable emulsion followed by polymerization. Particles are produced with can range in size from about 2 to about 600 nm.

In another embodiment, inorganic nanoparticles are used. Inorganic nanoparticles generally exist as oxides, silicates, carbonates and hydroxides. Some layered clay minerals and inorganic metal oxides can be examples of nanoparticles. The layered clay minerals suitable for use in the present invention include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite and vermiculite. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

Layered clay minerals may be either naturally occurring or synthetic. An example of one non-limiting embodiment of the coating composition uses natural or synthetic hectorites, montmorillonites and bentonites. Another embodiment uses the hectorites clays commercially available, and typical sources of commercial hectorites are the LAPONITEs from Southern Clay Products, Inc., U.S.A; Veegum Pro and Veegum F from R. T. Vanderbilt, U.S.A.; and the Barasyms, Macaloids and Propaloids from Baroid Division, National Read Comp., U.S.A.

In another embodiment, the nanoparticles comprise a synthetic hectorite a lithium magnesium silicate. One such suitable lithium magnesium silicate is LAPONITE, which has the formula:

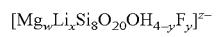

$[Mg_wLi_xSi_8O_{20}OH_{4-y}F_y]^{z-}$ wherein w=3 to 6, x=0 to 3, y=0 to 4, z=12−2w−x, and the overall negative lattice charge is balanced by counter-ions; and wherein the counter-ions are selected from the group consisting of selected $Na^+$, $K^+$, $NH_4^+$, $Cs^+$, $Li^+$, $Mg^{++}$, $Ca^{++}$, $Ba^{++}$, $N(CH_3)_4^+$ and mixtures thereof. (If the LAPONITE™ is "modified" with a cationic organic compound, then the "counter-ion" could be viewed as being any cationic organic group (R).)

Other suitable synthetic hectorites include, but are not limited to isomorphous substitutions of LAPONITE such as, LAPONITE B, LAPONITE S, LAPONITE XLS, LAPONITE RD, LAPONITE XLG, and LAPONITE RDS.

The nanoparticles may also be other inorganic materials, including inorganic oxides such as, but not limited to, titanium oxide silica, zirconium oxide, aluminum oxide, magnesium oxide and combinations thereof. Other suitable inorganic oxides include various inorganic oxides of alumina and silica. Another embodiment uses the aquasol colloidal silica, commercially available from Silco International, Inc., U.S.A, for example, SI1540, SI515, HP1540, and the colloidal silica BINDZIL, for example, Bindzil 30/360, Bindzil 40/220, commercially available from Eka-AkzoNobel Another embodiment of colloidal silica oxides use as nanoparticles is the dispersed fumed silica cluster of nanoparticles sold under the tradename AEROSIL, for example, Aerosil 7520, by Degussa. In yet another embodiment, surface-modified colloidal silica nanoparticles are used, for example, aluminum modified, BINDZIL 257/360, and BINDZIL DP5110, commercially available from Eka-AkzoNobel; and epoxy surfaced modified colloidal silica, BINDZIL CC30, and BINDZIL CC40, commercially available from Eka-AkzoNobel. Colloidal silica nanoparticles, are commercially available as stable dispersions often in water, for example, aquasols, with different stabilizing counterions, for example, sodium, and ammonium, and other stabilizing salts/ionic strength, e.g. sodium sulfate, sodium chloride, and in different solvents, for example, acetone, methanol. All forms of the stabilized colloidal silica and non-water dispersant carrier fluid are embodied in the use of colloidal silica nanoparticles or clusters of nanoparticles of this invention.

In another embodiment the nanoparticles comprise a Boehmite alumina ($[Al(O)(OH)]_n$) which is a water dispersible, inorganic metal oxide that can be prepared to have a variety of particle sizes or range of particle sizes, including a mean particle size distribution from about 2 nm to less than or equal to about 750 nm. For example, a boehmite alumina nanoparticle with a mean particle size distribution of around 25 nm under the trade name Disperal P2™ and a nanoparticle with a mean particle size distribution of around 140 nm under the trade name of Dispal® 14N4-25 are available from North American Sasol, Inc. In another embodiment the nanoparticles comprise colloidal silica sold under the trade name "SI 1540" by Silco International.

In another embodiment, the nanoparticles may be non-spherical, for example, nanoshells, nanowire, nanotubes, nanofiber, and porous nanoparticles such as aerogels.

Use of mixtures of nanoparticles in the hydrophilic coating compositions is also within the scope of the present disclosure.

In one embodiment the nanoparticles are selected from the group consisting of titanium dioxide, Boehmite alumina, sodium magnesium lithium fluorosilicates and combinations thereof.

In one embodiment, the weight ratio of film forming polymer to nanoparticles in the durable hydrophilic coating compositions ranges from about 1:1 to about 1:30, in another embodiment from about 1:4 to about 1:19, and in yet another embodiment from about 1:10 to about 1:15.

Optional Components

The durable hydrophilic coating compositions may also include optional components such as a rheology modifier, a carrier, an organic solvent and adjunct ingredients. Optional components, when present, are typically employed in coating compositions at levels of from about 0.001% to about 99.9%, in another embodiment at levels of from about 0.01% to about 98%, and in yet another embodiment at levels of from about 0.1% to about 96%, by weight of the composition.

Suitable rheology modifiers include, but are not limited to, polysaccharides maltodextrins, natural gums, natural hydrocolloids, modified starches, and modified cellulosics, such as Xanthan gum, deacetylated Xanthan gum, Gellan gum, Diutan gum, Welan gum, Gum Arabic, Guar gum, Carrageenan, Pectin, Maltodextrins, Cellulose gums, Methylcellulose, Hydroxypropyl methylcellulose, Hydroxypropylcellulose, Hydroxypropyl guar, Guar hydroxypropyltrimonium chloride, Hydroxyethylcellulose, Cetyl hydroxyethylcellulose, cationic microfibril cellulose, anionic microfibril cellulose, Carbomer, copolymers of acrylic acid crosslinked with polyalkenyl polyether, acrylate crosspolymer, polyacrylate-1 crosspolymer, acrylate copolymer. According to certain embodiments, the rheology modifier, or combinations thereof, is present in an effective amount of from about 0.02%, 0.05%, 0.1% to about 0.3%, 0.4%, or 1.0%, by weight of the composition.

Suitable carriers include liquids, solids and gases. In one embodiment, the carrier is water, which can be distilled, deionized, or tap water. Water is valuable due to its low cost, availability, safety, and compatibility.

In another embodiment, in addition to or in place of water, the carrier can comprise a low molecular weight organic solvent. As one example, the solvent is highly soluble in water, for example, ethanol, methanol, acetone, ethylene glycol, propanol, isopropanol, and the like, and mixtures thereof.

Low molecular weight alcohols can reduce the surface tension of the nanoparticle dispersion to improve wettability of the substrate. This is particularly helpful when the substrate is hydrophobic. Low molecular weight alcohols can also help the treated substrate to dry faster. The optional water soluble low molecular weight solvent can be used at any suitable level. The carrier can comprise any suitable amount of the composition, including but not limited to from about 10% to about 99%, alternatively from about 30% to about 95%, by weight of the coating composition.

The coating compositions can contain other optional adjunct ingredients, including but not limited to, antimicrobial preservatives, antioxidants, anti-static agents, chelating agents, colorants, dyes, filler salts, fungicides, insect and moth repellant agents, germicides, hydrotropes, metallic salts. These optional ingredients may be included at any desired level, but are typically added at a level of from about 0.0001% to about 99.99% by weight of the composition.

The coating compositions can be applied to the substrate in any suitable manner. The coating compositions can be applied to the substrate when the substrate is at least partially immersed in a bath of the composition (immersive processes), or without immersing the substrate in the coating composition (non-immersive processes).

In one embodiment, the coating composition is applied by kiss-roll coating. In kiss-roll coating, the composition is kept in a suitable bath. A rotating cylinder or any other device suitable for this process, is contacting the composition with at least a part of its surface. Thus, the composition is spread on the surface of the cylinder. The substrate is brought into contact with the cylinder while the cylinder already has the composition spread on its surface. In this process, the amount of composition applied on the substrate can be controlled easily and it is possible to avoid soaking the substrate with composition.

Alternatively to the kiss-roll coating, the composition can also be sprayed on the surface of the plurality of fibers. Like the kiss-roll coating, spraying enables low and easily controllable add-on level of aqueous solution, which is preferred in the present invention. Other alternative methods include, but are not limited to, printing such as, rotary, gravure, flexographic printing, ink jet printing, slot coating and the like.

EXAMPLES

The following examples are given solely for the purpose of illustration and is not to be construed as limitations of the present invention, as many variations of the invention are possible without departing from the spirit and scope of the present disclosure. Examples 1-6 and 8-13 are durable hydrophilic coating compositions according to the present disclosure. Each of the compositions defined in Examples 1-6 and 8-13 is prepared by adding the components to water in the following order (while maintaining adequate mixing at room temperature): rheology modifier (if present), film forming polymer, wetting agent and nanoparticle.

TABLE 1

Durable Hydrophilic Coating Compositions

| Component, wt % | 1 | 2 | 3 | 4 | 5 | 6 | 7 |
|---|---|---|---|---|---|---|---|
| Film Forming Polymer[1] | 4.0 | 4.0 | 4.0 | 4.0 | 1.0 | 1.0 | |
| Wetting Agent[2] | 0.05 | 0.5 | 0.5 | 0.5 | 0.035 | 0.5 | |
| Rheology Modifier[3] | | | 0.3 | 0.1 | 0.1 | 0.1 | |
| Nanoparticle[4] | 16.0 | 16.0 | 16.0 | 16.0 | 19.0 | 19.0 | |
| Surfactant[5] | | | | | | | 8.0 |
| Water | quantity sufficient to 100% | | | | | | |

| Component, wt % | 8 | 9 | 10 | 11 | 12 | 13 | 14 |
|---|---|---|---|---|---|---|---|
| Film Forming Polymer[1] | 0.025 | 0.05 | 0.25 | 0.1 | 0.05 | 0.1 | |
| Wetting Agent[2] | 0.02 | 0.02 | 0.05 | 0.005 | 0.02 | 0.9 | |
| Nanoparticle[4] | 0.475 | 0.95 | 0.25 | 0.4 | 0.45 | 0.9 | |
| Surfactant[6] | | | | | | | 10.0 |
| Water | quantity sufficient to 100% | | | | | | |

[1]FLEXAN II is a sodium polystyrene sulfonate available from National Starch
[2]DYNOL 604 is a nonionic surfactant available from Air Products and Chemical, Inc.
[3]Xanthan Gum
[4]SILCOL 1540 is a colloidal silica available from Silco International, Inc.
[5] PHP-26 is an aqueous cationic/amphoteric emulsion containing a modified silicone polyether and alkyl surfactants available from Schill & Seilacher.
[6]Stantex 6327 available from Pulcra Chemicals The test methods and apparatuses described below may be useful in testing embodiments of the present disclosure. Unless otherwise stated, all tests are performed under standard laboratory conditions (50% humidity and at 73° F. (23° C.)).

1. Surface Tension Reduction

The surface tension (unit: mN/m) is determined according to the following test, which is based on ASTM D-1331—Standard Test Method for Surface and Interfacial Tension of Solutions of Surface Active Agents.

The following equipment is used to determine surface tension reduction:

Tensiometer: A K10 tensiometer provided by Kruiss GmbH, Germany or equivalent. The vessel elevation speed should be 4 mm/min. Liquid surface height should be sensed automatically when using a plate or a ring. The equipment must be able to adjust the sample position automatically to the correct height. Precision of test should be +/−0.1 mN/m.

Pt-Ring
Pt-Plate
50 ml beaker
Hydraulic Press/Cutter: A hydraulic press/cutter such as the Alpha Cutter or equivalent available from Thwing-Albert Frank GmbH, Germany.
Die with soft foam 60 mm×60 mm with an accuracy and precision of ±1 mm available from Ottenser Modell & Formenbau GmbH, Germany
Balance Procedure (i) Calibration: Pour 40 ml of saline (0.9 wt % NaCl in deionized water) into a clean beaker. Test the surface tension of the saline with a platinum ring or a platinum plate using the method described in equipment instructions. The surface tension should be 71-72 mN/m at 20° C. (ii) Preparation: Clean the beaker with deionized water, followed by a thorough rinsing in fresh 2-Propanol, including burning it out with a gas burner for a few seconds. Let the beaker cool to room temperature before using. Clean the Platinum plate or ring by rinsing thoroughly in 2-Propanol and in distilled water. Allow the plate/ring to dry, and then heat to a slight red with a gas burner. Allow the plate/ring to cool to room temperature. Cut 10 6×6 mm samples of nonwoven with a punch-knife. (iii) Test: Put 40 ml of test-liquid (0.9% Sodium Chloride solution based on EDANA—European Disposables And Nonwovens Association—150) into the beaker. Place the 60×60 mm sample on top of the beaker, dip the sample into the test-liquid using a clean surfactant-free plastic stick and stir for 10 seconds. Leave the stick in the beaker and let the solution with sample stand for 5 minutes. Stir again by hand for ten seconds. Remove the sample from the test-liquid with the stick or tweezers. Let the test-liquid stand for ten minutes. Then measure the surface tension of the test-liquid using the Wilhelmy plate method of Du Nuoy method using the method described in the equipment instructions. The measured surface tension is the wash-off surface tension. The beaker and Pt-plate or Pt-ring need to be cleaned as described above before any additional samples are measured. Run agreed number of samples, i.e. 10.

Exemplary Surface Tension Reduction ("STR") results for SMS nonwoven materials (10 gsm available from Fibertex under the product no. H20201010) coated with the durable hydrophilic coating compositions of Examples 1-14 of Table 1 are reported in Table 2. The values reported in Table 2 are the average of the absolute values for each set of 10 samples. For Examples 1-4 and 6-7 the coating composition was applied to the nonwoven by kiss-roll coating, squeezed and oven dried. For Examples 8-9 and 11-14, the coating composition was applied to the nonwoven by an immersive process, squeezed and oven dried. The STR for water is 72.8 mN/m.

TABLE 2

| Durable Hydrophilic Coating Compositions | STR (10 swatch) (mN/m) | Δ STR from water (mN/m) | % Δ STR from water |
|---|---|---|---|
| 1 | 72.6 (±0.03) | 0.2 | 0.3 |
| 2 | 62.4 (±0.26) | 10.4 | 16.7 |
| 3 | 65.3 (±0.22) | 7.5 | 11.5 |
| 4 | 68.2 (±0.21) | 4.6 | 6.7 |
| 6 | 71.9 (±0.15) | 0.9 | 1.3 |
| 7 | 34.6 | 38.2 | 110.4 |
| 8 | 52.6 | 20.2 | 38.4 |
| 9 | 55.3 | 0.2 | 31.6 |
| 11 | 69.4 | 3.4 | 4.9 |
| 12 | 51.3 | 21.5 | 41.9 |
| 13 | 53.9 | 18.9 | 35.1 |
| 14 | 52 | 20.8 | 40.0 |

As can be seen in Table 2, in one embodiment exemplary coating compositions have a % Δ STR from water of from about 0% to about 30%, in another embodiment of from about 0% to about 10% and in yet another embodiment of from about 0% to about 5%.

2. Liquid Strike-Through Test

The liquid strike-through time is measured using Lister-type strike-through equipment, manufactured by Lenzing AG, Austria. Test procedure is based on standardized EDANA method 150.3-96, with the test sample placed on an absorbent pad comprised of ten plies of filter paper (Ahlstrom Grade 989 obtained from Empirical Manufacturing Co., Inc., or equivalent). In a typical experiment five consecutive 5 ml gushes of test liquid (18 g of sodium chloride diluted to 2 liters with deionized water, stirring for approximately 5 minutes with a magic bar) are applied to a nonwoven sample at one minute intervals and the respective strike-through times are recorded without changing the absorbent pad.

Figure 7:
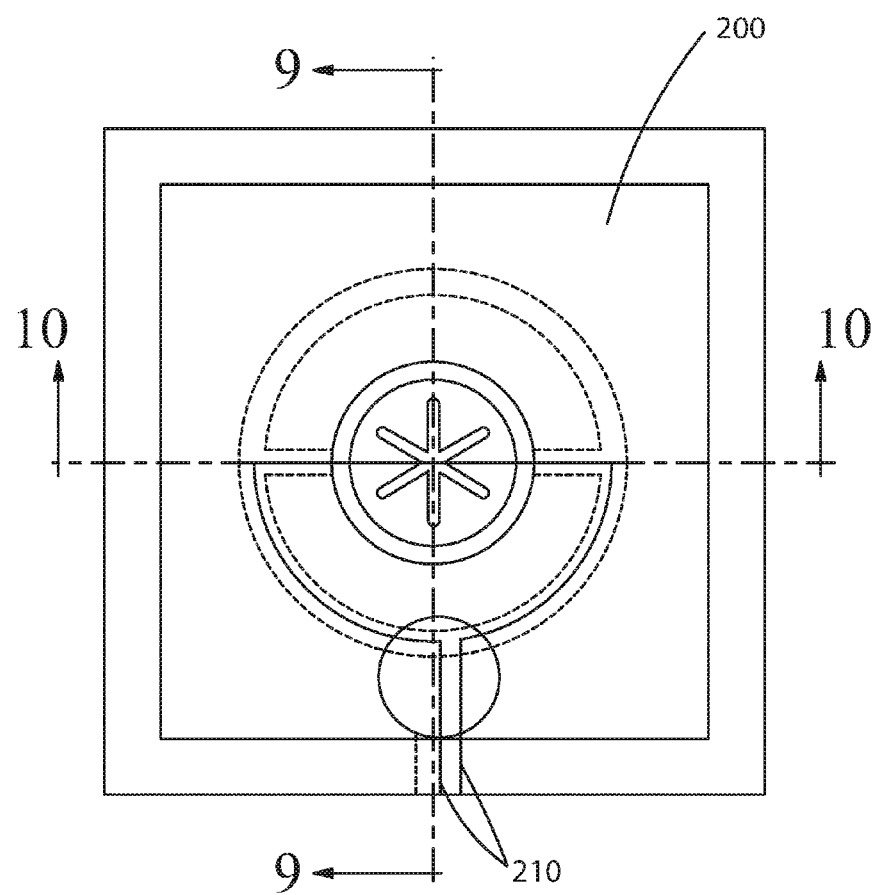
FIG. 7 is a schematic top view of a strike-through plate which may be used to measure Liquid Strike-through of a substrate in accordance with an embodiment of the present disclosure.
Figure 8:
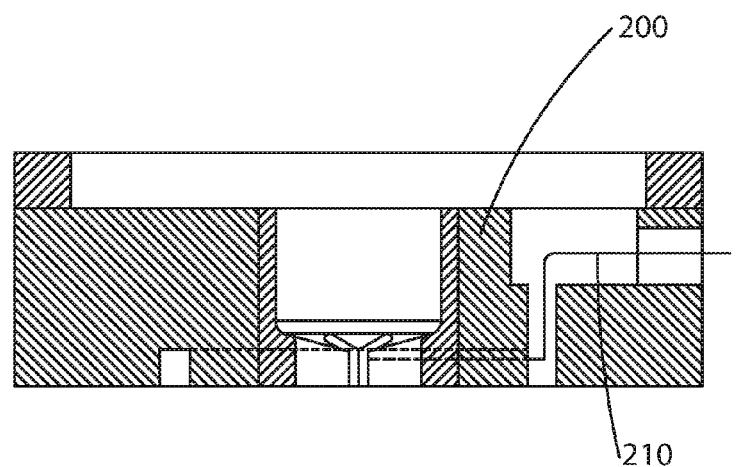
FIG. 8 is a sectional view along 9-9 of the strike-through plate of FIG. 7.
Figure 9:
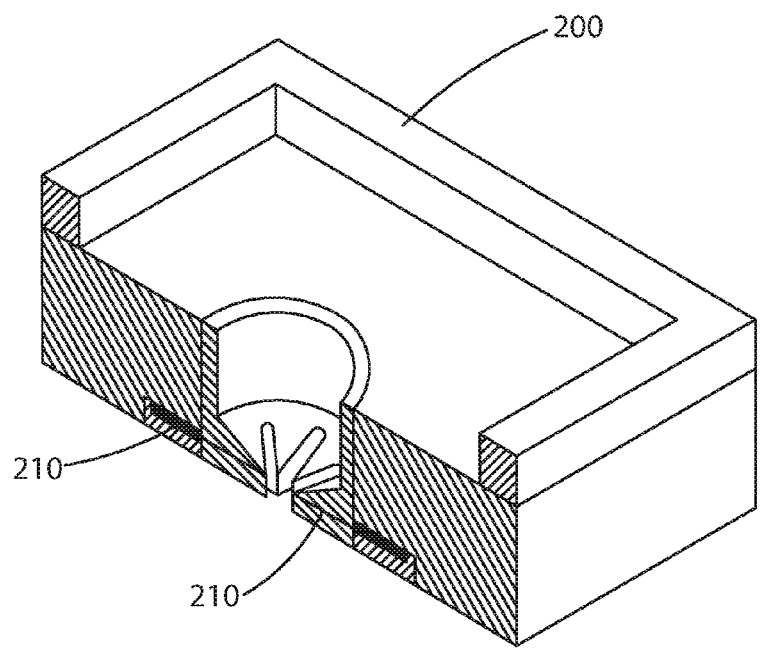
FIG. 9 is a sectional perspective view along 10-10 of the strike-through plate of FIG. 7.

The following equipment is used for the Liquid Strike-Through Test:

Lister Strike-through Equipment: (i) base unit with electronic timer measuring to 0.01 seconds and automatic funnel with a rate of discharge of 25 ml in 3.5 (±0.25) seconds; (ii) Strike-through plate constructed of 25 mm thick acrylic glass. The total weight of the plate must be 500 g. The electrodes should be of non-corrosive material. The electrodes are set in (4.0 mm×7.0 mm) cross section grooves, cut in the base of the plate and fixed with quick setting epoxy resin. FIGS. 7, 8, and 9 illustrate a Strike-through plate 200 containing electrodes 210. FIG. 7 is a top view of a Strike-through plate 200, where as FIG. 8 is a sectional view along 9-9 of the Strike-through plate 200 of FIG. 7. FIG. 9 is a sectional perspective view along 10-10 of the Strike-through plate 200 of FIG. 7; (iii) Base plate constructed of a square of acrylic glass 125 mm×125 mm; (iv) Ring stand to support the funnel; (v) Burette with 50 ml capacity; and (vi) Core filter paper Ahlstrom Grade 989 or equivalent (average Strike-through time 1.7 s±0.3 s, dimensions: 10×10 cm).

Procedure: (1) Cut the required number of samples, 12.5 cm×12.5 cm, touching the sample only at the edge of the sample. (2) Weigh 10 plies of core filter paper and place one sample on the set of 10 plies of filter paper on the base plate. The sample should be positioned on the filter paper in such a way that the side of the nonwoven, which is intended to face the user's skin (when applied in an absorbent article) is uppermost. (3) Place the strike-through plate on top with the center of the plate over the center of the test piece. Center the burette and the funnel over the plate. (4) Ensuring that the electrodes are connected to the timer, switch on the timer and set the clock to zero. (5) Fill the burette with test liquid. Keep the discharge valve of the funnel closed and run 5.0 ml of liquid (=one gush) from the burette into the funnel. (6) Open the magnetic valve of the funnel to discharge 5.0 ml of liquid. The initial flow of liquid will complete the electrical circuit and start the timer. It will stop when the liquid has penetrated into the pad and fallen below the level of the electrodes in the strike-through plate. (7) Record the time indicated on the electronic timer. (8) Wait 60 seconds and repeat steps (4), and (6) to (9) for the second, the third gush and any subsequent gush, with each gush comprising 5 ml of liquid. (e.g., 5 ml into funnel, open magnetic valve, etc.) Record the Time for the $1^{st}$, $2^{nd}$, and any subsequent gush in seconds.

Exemplary Strike-through results for SMS nonwoven materials (10 gsm available from Fibertex under the product no. H20201010) coated with the durable hydrophilic coating compositions of Examples 1-13 of Table 1 are reported in Table 3. For Examples 1-7 the coating composition was applied to the nonwoven by kiss-roll coating, squeezed and oven dried. For Examples 8-14, the coating composition was applied to the nonwoven by an immersive process, squeezed and oven dried.

TABLE 3

| | Strike-through Time (seconds) | | | |
|---|---|---|---|---|
| Durable Hydrophilic Coating Compositions | $1^{st}$ Gush | $3^{rd}$ Gush | $5^{th}$ Gush | % Δ ($1^{st}$ – $5^{th}$) |
| 1 | 56.7 (>100 for n = 2) | 34.7 (>100 for n = 2) | 59.3 (>100 for n = 2) | 4.6 |
| 2 | 6.1 (±1.1) (>100 for n = 1) | 13.5 (±3.1) (>100 for n = 1) | 12.6 (±9.1) | 106.6 |

TABLE 3-continued

| | Strike-through Time (seconds) | | | |
|---|---|---|---|---|
| Durable Hydrophilic Coating Compositions | 1$^{st}$ Gush | 3$^{rd}$ Gush | 5$^{th}$ Gush | % Δ (1$^{st}$ – 5$^{th}$) |
| 3 | 3.7 (±0.93) | 5.4 (±0.62) | 4.3 (±0.7) | 16.2 |
| 4 | 10.2 (±1.3) | 32.6 (±23.8) | 22.1 (±12.5) | 116.7 |
| 5 | 5.6 (±0.94) | 6.1 (±1.3) | 5.8 (±1.9) | 3.6 |
| 6 | 11.2 (±5.7) | 13.8 (±11.9) | 16.9 (±17.6) | 50.9 |
| 7 | 1.8 | 4.8 | 4.8 | 166.7 |
| 8 | 1.8 | 2.4 | 2.5 | 38.9 |
| 9 | 1.6 | 2.2 | 2.0 | 25.0 |
| 10 | 1.5 | 2.4 | 2.0 | 33.3 |
| 11 | 1.6 | 2.0 | 1.8 | 12.5 |
| 12 | 1.7 | 2.5 | 1.7 | 0.0 |
| 13 | 1.7 | 2.4 | 1.9 | 11.8 |
| 14 | 2.5 | 6.3 | 4.6 | 84.0 |

As can be seen in Table 3, in one embodiment exemplary coating compositions have a % Δ of from about 0% to about 40%, in another embodiment of from about 0% to about 30% and in yet another embodiment of from about 0% to about 20%.

3. Time-of-Flight Secondary Ion Mass Spectrometry (ToF-SIMS)

Investigation of the surface chemistry of solid materials, including, but not limited to nonwovens, can be accomplished using time-of-flight secondary ion mass spectrometry (ToF-SIMS). ToF-SIMS utilizes a focused, energetic ion beam (referred to as "primary ions") to sputter material from the samples surface. Primary ions include, but are not limited to, $Ar^+$, $Xe^+$, $Cs^+$, $Ga^+$, $In^+$, $Au_m^+$, and $Bi_m^+$ in an energy range including, but not limited to, 10 keV to 25 keV. Some of the sputtered material is ionized (referred to as "secondary ions"), and is mass-analyzed and detected in a mass spectrometer, including, but not limited to, a single-stage reflectron time-of-flight mass spectrometer. Sample damage during analysis is minimized by maintaining a primary ion dose below the static limit of $10^{12}$ primary ions/cm$^2$.

For electrically insulating samples such as nonwovens, charge compensation is accomplished using a low energy electron flood gun. In this method, a ToF-SIMS IV instrument (Ion-Tof GmbH, Munster, Germany) equipped with a 25 keV $Bi_3^+$ primary ion sources and low energy electron flood gun is used. Mass calibration of mass spectra is accomplished using the $CH_3^+$ (m/z=15), $C_2H_3^+$ (m/z=27), and $C_3H_5^+$ (m/z=41) peaks in the positive ion mode and $CH^-$ (m/z=13), $OH^-$ (m/z=17), and $C_2H^-$ (m/z=25) in the negative ion mode.

Procedure: Analysis of solid materials including, but not limited to, nonwoven materials using ToF-SIMS is accomplished by cutting approximately 1 cm×1 cm samples from the solid material, mounting the sample using double-sided adhesive tape onto an appropriate sample stub, and introduction of the sample into the ToF-SIMS instrument for analysis. Identification of chemical materials on the sample surface including, but not limited to, surfactants and polymers, can be accomplished by comparison of the mass spectra obtained from the sample to reference spectra obtained from the materials deposited onto the sample. This method is used to verify the surface modification of a nonwoven material or test for dry migration of surfactants onto neighboring materials.

Figure 10:
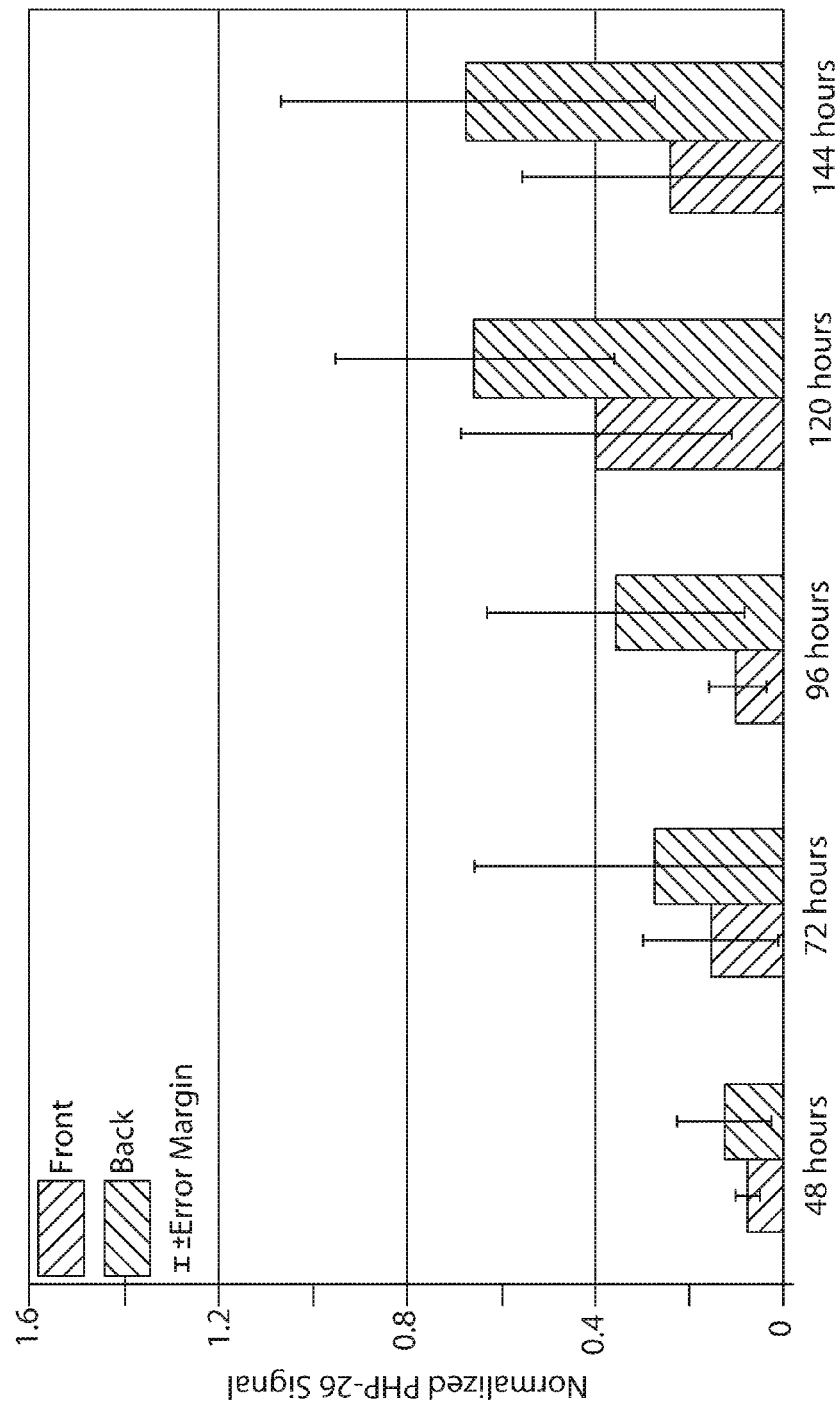
FIG. 10 sets forth dry migration data as measured by ToF-SIMS for a conventional surfactant.

FIG. 10 sets forth in graph form the dry migration data as measured by ToF-SIMS for a conventional surfactant. This dry migration data is also shown below in Table 4. The reference sample shown in FIG. 10 was layered as follows: cuff (957276680, BBA Fiberweb 17 gsm); topsheet (95411467, BBA Fiberweb 14.9 gsm); corecover (64007551, Avgol 10 gsm containing PHP-26); dusting layer (11 gsm SMMS coated with PHP-26); dusting layer (11 gsm SMMS); and corecover (64007551, Avgol 10 gsm containing PHP-26). PHP-26 surface concentrations on the nonwoven layers were monitored using the ratio of the $C_3H_8N^+$ (m/z=58) secondary ion intensity to the $C_3H_7^+$ (m/z=43) secondary ion intensity in the positive ion mode ToF-SIMS data. The results of the ToF-SIMS analysis shows migration of PHP-26 to the cuff reached a steady state after 120 hours. With reference to FIG. 10, "front" is the side away from the topsheet. "Back" is the side facing the topsheet. PHP-26 signal is always higher on the topsheet side of the cuff than the side facing away from the topsheet. PHP-26 signal increased with time. 120 hours of aging was required to reach steady state. Samples were aged in a 60 degree C. oven.

TABLE 4

| | Normalized PHP-26 Signal (average) | |
|---|---|---|
| Storage Time (hours) | (Front) | (Back) |
| 48 | 0.08 ± 0.02 | 0.13 ± 0.10 |
| 72 | 0.16 ± 0.14 | 0.28 ± 0.38 |
| 96 | 0.10 ± 0.06 | 0.36 ± 0.27 |
| 120 | 0.41 ± 0.29 | 0.67 ± 0.30 |
| 144 | 0.25 ± 0.31 | 0.69 ± 0.40 |

Figure 11:
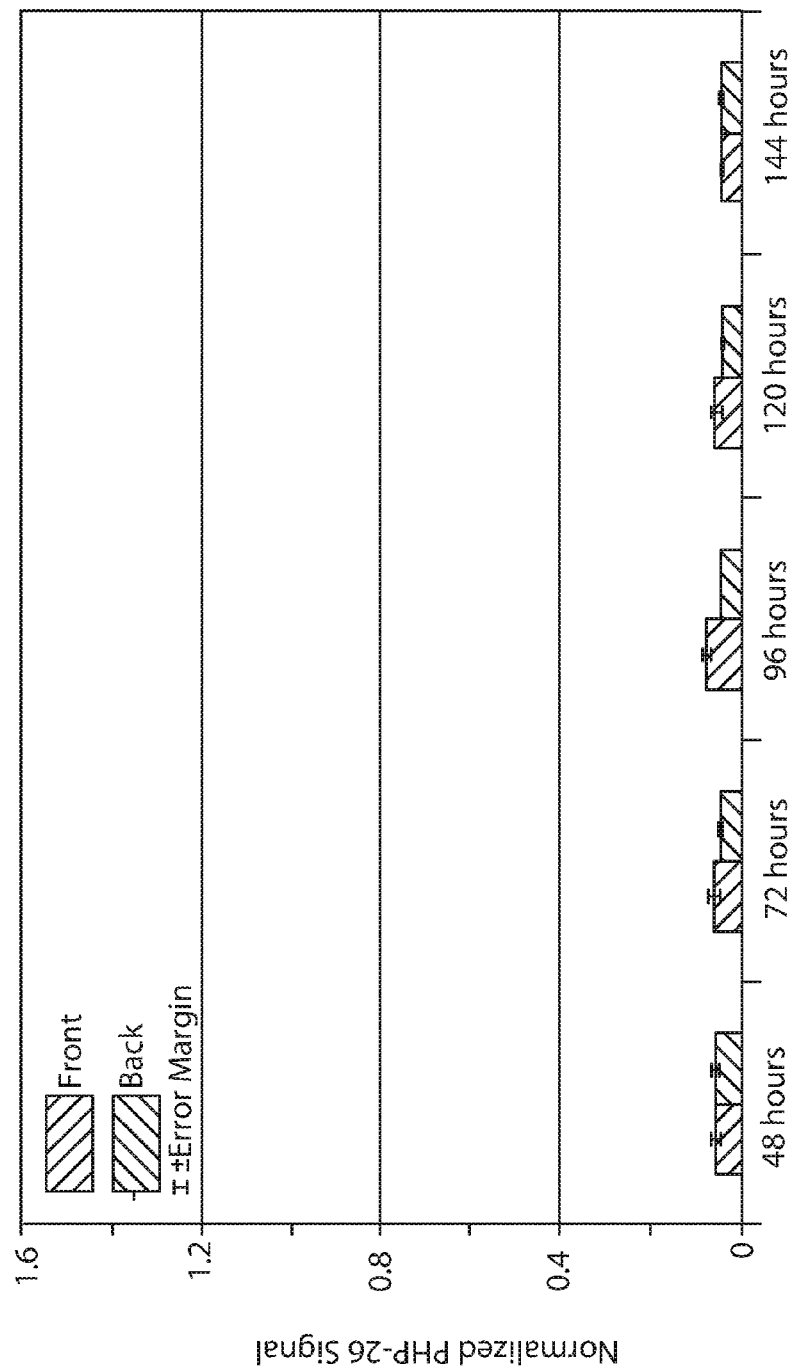
FIG. 11 sets forth dry migration data as measure by ToF-SIMS for a durable hydrophilic coating composition in accordance with an embodiment of the present disclosure.

FIG. 11 sets forth in graph form the dry migration data as measure by ToF-SIMS for a durable hydrophilic coating composition in accordance with an embodiment of the present disclosure. This dry migration data is also shown below in Table 5. The reference sample shown in FIG. 11 was layered as follows: cuff (957276680, BBA Fiberweb 17 gsm); topsheet (95411467, BBA Fiberweb 14.9 gsm); dusting layer (11 gsm SMMS coated with durable hydrophilic composition of Example 3 in Table 1); corecover (64007551, Avgol 10 gsm containing PHP-26); (64007551, Avgol 10 gsm containing PHP-26); and dusting layer (11 gsm SMMS coated with durable hydrophilic composition of Example 3 in Table 1). The results of the ToF-SIMS analysis shows that the PHP-26 signal was low across the sample, indicating that there was no migration of PHP-26 to the cuff. With reference to FIG. 11, "front" is the side away from the topsheet. "Back" is the side facing the topsheet. Topsheet surfactant (Stantex™ 6627) was not detected on the cuff. Samples were aged in a 60 degree C. oven.

TABLE 5

| Storage Time (hours) | Normalized PHP-26 Signal (average) | |
| --- | --- | --- |
| | (Front) | (Back) |
| 48 | 0.05 ± 0.01 | 0.05 ± 0.01 |
| 72 | 0.06 ± 0.01 | 0.05 ± 0.00 |
| 96 | 0.08 ± 0.01 | 0.05 ± 0.00 |
| 120 | 0.06 ± 0.01 | 0.05 ± 0.00 |
| 144 | 0.05 ± 0.00 | 0.05 ± 0.01 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising an absorbent core, the absorbent core comprising:
   (a) a storage layer; and
   (b) a hydrophilic fluid pervious core wrap, the core wrap surrounding at least a portion of the storage layer, wherein the core wrap comprises:
      i. a core wrap substrate; and
      ii. a durable hydrophilic coating composition coated on the core wrap substrate, the coating composition comprising a film forming polymer, a wetting agent, and from about 0.001% to about 40%, by weight of the composition, of nanoparticles wherein the nanoparticles are selected from the group consisting of alumina, silica and combinations thereof and wherein the nanoparticles have a particle size of from about 1 to about 750 nanometers;
   wherein the weight ratio of the film forming polymer to the nanoparticles is from about 1:1 to about 1:30.

2. The disposable absorbent article according to claim 1, wherein the core wrap substrate comprises a top layer and a bottom layer.

3. The disposable absorbent article according to claim 2, wherein the core wrap substrate surrounds all of the storage layer.

4. The disposable absorbent article according to claim 1, wherein the film forming polymer is selected from the group consisting of polyacrylates, polyacrylic acid ester, polyurethanes, polystyrene, polystyrene sulfonate, polyvinyl acetate, polyvinyl alcohol, polymethacrylates, polyphenol, polyesters, sulfopolyesters, cellulose and derivatives thereof, starch and derivatives thereof, and copolymers thereof.

5. The disposable absorbent article according to claim 4, wherein the film forming polymer is selected from the group consisting of sodium polystyrene sulfonate, polyvinylpolypyrrolidone, polyvinylimine, xanthan gum, and hydropropylcellulose.

6. The disposable absorbent article according to claim 5, wherein the film forming polymer is sodium polystyrene sulfonate.

7. The disposable absorbent article according to claim 1, wherein the film forming polymer is present in an amount from about 0.1% to about 60%, by weight, of the composition.

8. The disposable absorbent article according to claim 7, wherein the film forming polymer is present in an amount from about 1% to about 30%, by weight, of the composition.

9. The disposable absorbent article according to claim 8, wherein the film forming polymer is present in an amount from about 5% to about 20%, by weight, of the composition.

10. The disposable absorbent article according to claim 1, wherein the wetting agent is selected from the group consisting of anionic surfactants, cationic surfactants, nonionic surfactants, zwitterionic surfactants and combinations thereof.

11. The disposable absorbent article according to claim 10, wherein the wetting agent is a nonionic surfactant.

12. The disposable absorbent article according to claim 1, further comprising a rheology modifier selected from the group consisting of polysaccharides, maltodextrins, natural gums, modified starches and combinations thereof.

13. The disposable absorbent article according to claim 12, wherein the rheology modifier is xanthan gum.

* * * * *